United States Patent [19]

Fatches

[11] Patent Number: 4,483,825
[45] Date of Patent: Nov. 20, 1984

[54] PIPETTE AND FILTER COMBINATION

[76] Inventor: Keith R. Fatches, 6 Crewe St., Bardwell Park, New South Wales, 2207, Australia

[21] Appl. No.: 396,563

[22] Filed: Jul. 9, 1982

[51] Int. Cl.³ .................. B01L 3/02; B01D 33/00; G01N 1/12
[52] U.S. Cl. .................. 422/100; 73/864.01; 210/927; 422/101; 436/178; 604/190
[58] Field of Search .................. 422/100, 101, 99; 436/177, 178; 128/763, 765, 767; 210/518, 923, 359, 927; 604/187, 190, 212, 216, 231; 73/864.02, 864.03, 864.11, 864.01

[56] References Cited

U.S. PATENT DOCUMENTS

| 3,512,940 | 5/1970 | Shapiro | 604/190 X |
| 3,635,218 | 1/1972 | Ericson | 128/231 |
| 3,846,077 | 11/1974 | Ohringer | 422/100 |
| 4,266,559 | 5/1981 | Akhavi | 73/864.02 X |

Primary Examiner—Barry S. Richman
Assistant Examiner—Michael S. Gzybowski
Attorney, Agent, or Firm—Ladas & Parry

[57] ABSTRACT

A pipette having a liquid receiving hollow generally encompassed by deformable side walls, the pipette further has a tapered liquid outlet extending from one end of the hollow and a liquid inlet on the other end of the hollow within which is located a semi-permeable filter.

4 Claims, 5 Drawing Figures

PIPETTE AND FILTER COMBINATION

The present invention relates to pipettes.

It is a disadvantage of known methods of separating the blood cells from plasma in centrifuged blood samples in that the plasma must be either tipped or pipetted off the cells into another receptacle.

It is an object of the present invention to overcome or substantially ameliorate the above disadvantages.

There is disclosed herein a pipette having a liquid receiving hollow generally encompassed by deformable side walls, a tapered liquid outlet extending from one end of said hollow, and a liquid inlet on the other end of said hollow and a filter located in said inlet.

A preferred form of the present invention will now be described by way of example with reference to the accompanying drawings, wherein:

FIG. 1 is a schematic sectioned side elevation of a pipette having a filter inlet;

FIG. 2 schematically depicts use of the pipette of FIG. 1;

Figure 1:
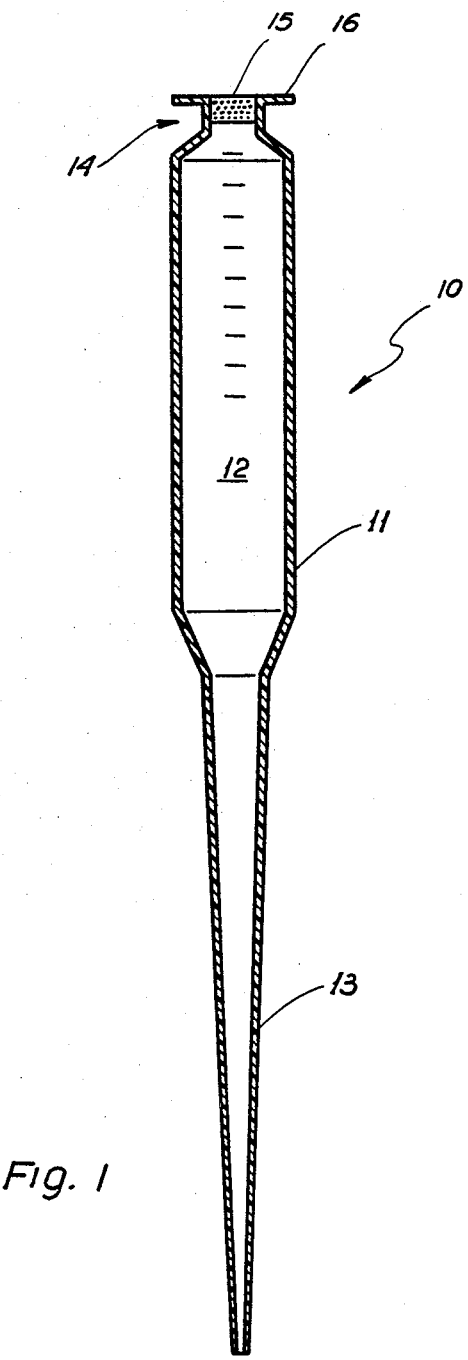

In FIG. 1 there is schematically depicted a pipette 10 having a main body 11 defining a calibrated hollow 12 which receives a liquid to be dispensed by the pipette 10. Extending from the body 11 is a tapered tip 13 which is adapted to accurately dispense the liquid contained in the hollow 12. The other end of the body 11 is provided with a neck 14 within which is received a filter 15. Additionally, the body 11 is provided with a flexible seal 16. The pipette 10 is to be made of plastics material so that the body 11 may be resiliently deformed to cause the liquid to exit through the tip 13.

In practice the body 11 would be squeezed by the fingers of a user of the pipette 10 in order to cause the liquid to exit via the tip 13. Additionally the seal 16 should be flexible enough to resiliently sealingly engage against the internal surface of a test tube.

Figure 2:
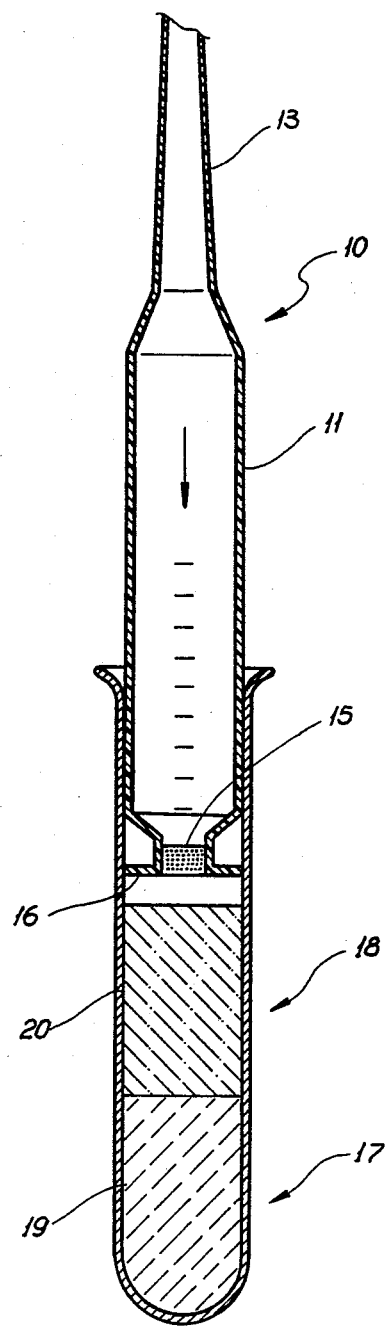

Now also with reference to FIG. 2 there is schematically depicted a test tube 17 through which is received a sample of blood 18 which has been subjected to centrifugal force to cause the sample 18 to separate due to density differences into two liquids or phases 19 and 20. In the present instance the liquid or phase 20 would be a plasma and phase 19 is compacted blood cells. In order to extract the plasma 20 from within the test tube 17, the pipette 10 would be inserted in the test tube 17 so that the seal 16 would resiliently sealingly engage the internal surfaces of the test tube 17.

The pipette 10 would be further moved so as to bear against the plasma 20 and therefore force the plasma 20 to enter the body 11 of the pipette 10 via the seal 15. Upon sufficient quantity of the plasma 20 being received within the body 11, the body 11 need only be resiliently deformed in order to dispense the plasma 20 via the tip 13.

Figures 3, 4, 5:
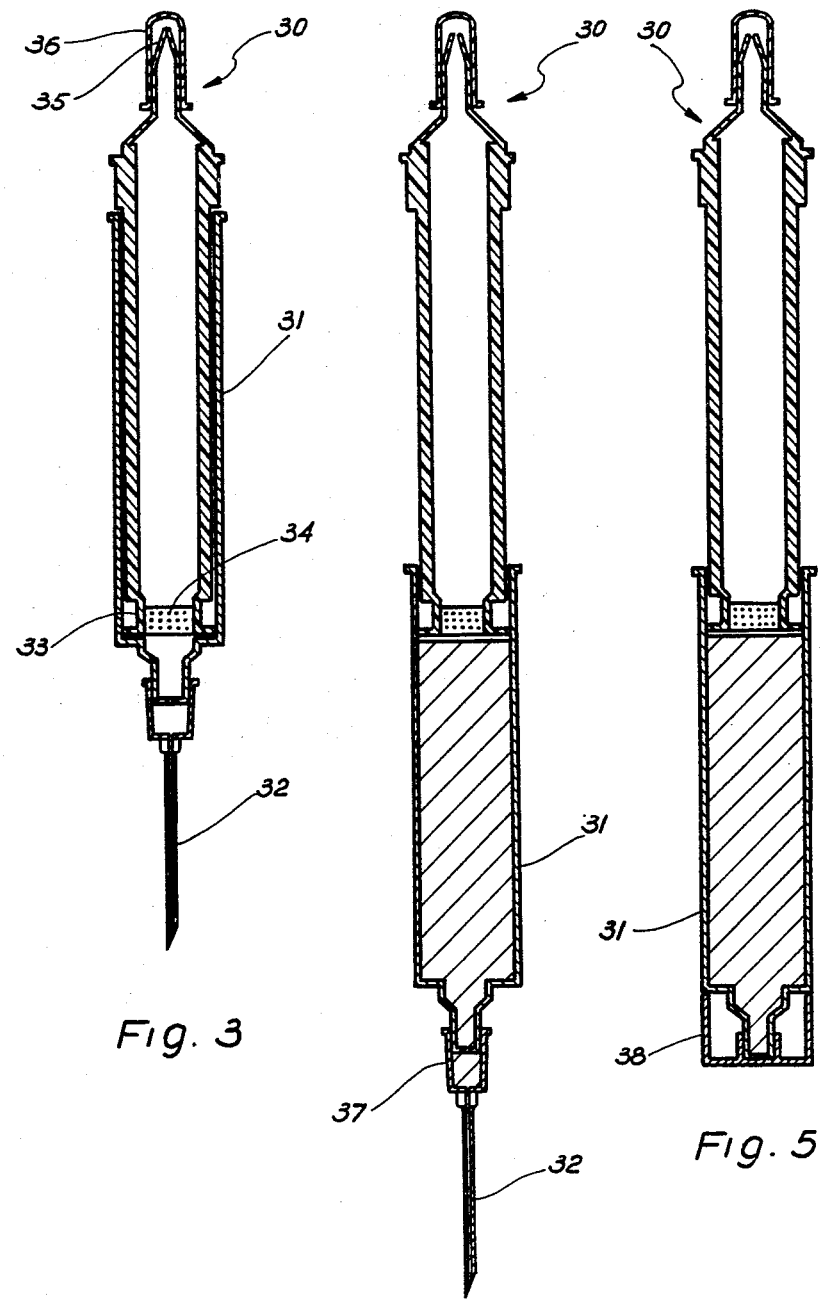
FIG. 3 is a schematic sectioned side elevation of the pipette of FIG. 1 adapted to be used in combination with a syringe body.
FIG. 4 is a schematic sectioned side elevation of the pipette and syringe assembly of FIG. 3 extended so as to receive a blood sample.
FIG. 5 is a schematic sectioned side elevation of the syringe and pipette of FIG. 3 with the needle of the syringe removed.

Referring now to FIGS. 3 to 5 wherein the pipette of FIGS. 1 and 2 is depicted as co-operating with the body of the syringe. As can be seen the pipette 30 sealingly co-operates with a syringe body 31 which terminates with a needle 32. The pipette 30 is basically the same construction as the pipette of FIGS. 1 and 2 in that the liquid inlet end 33 is provided with a filter 34, preferably a semi-permeable membrane. The other end of the pipette 30 is provided with a sealing cap 36. Additionally the needle 32 and mounting 37 therefor is removable from the syringe body 31 so that a sealing cap 38 is sealingly locatable on the inlet extremity on the syringe body 31.

In operation of the above described pipette and syringe assembly, blood is drawn into the syringe by telescopic outward movement of the pipette 30 from within the syringe body 31. Thereafter the needle 32 is removed and the cap 38 placed on the inlet end of the body 31 so as to sealingly close the inlet. The pipette 30 and syringe body 31 is then centrifuged so as to separate the blood cells from the plasma. To then remove the plasma from within the syringe body 31, the cap 36 is removed and the pipette telescopically removed within the syringe body 31 so as to locate the plasma within the interior of the pipette 30. The plasma may then be dispensed from within the pipette 30 by resiliently deforming the side walls of the pipette 30 to expel the plasma from the tapered outlet 35.

Preferably the pipette 30 would be formed of resilient plastics material to allow resilient deformation of the walls to expel the plasma from within the pipette. Additionally the pipette 30 may need to be reinforced by resilient ribs so that it may successfully operate as a piston when co-operating with the internal surfaces of the syringe body 31.

What I claim is:

1. A pipette for separating plasma from a centrifuged blood sample comprising a hollow tubular member terminating at opposite ends and constructed of a resilient, deformable material, a liquid inlet at one end of said hollow tubular member, and a semi-permeable filter located in said inlet wherein said filter permits only plasma to pass therethrough and enter into said hollow tubular member while preventing blood cells from entering said hollow tubular member, and a tapered liquid outlet extending from the other end of said hollow tubular member through which said filtered plasma is expelled by resilient deformation of the hollow tubular member.

2. The pipette of claim 1 wherein said liquid inlet has a peripheral surface dimension to slidingly sealingly co-operate with the internal surface of a test tube.

3. In combination, a pipette and syringe for separating plasma from a centrifuged blood sample, said pipette being received by the syringe for sealed telescopic relative motion therein and said pipette comprising a hollow tubular member terminating at opposite ends and constructed of a resilient, deformable material, a liquid inlet at one end of said hollow tubular member, and a semi-permeable filter located in said inlet wherein said filter permits only plasma to pass therethrough and enter into said hollow tubular member while preventing blood cells from entering said hollow tubular member, and a tapered liquid outlet extending from the other end of said hollow tubular member through which the filtered plasma is expelled by resiliently deforming said hollow tubular member.

4. The pipette and syringe combination of claim 3 wherein said pipette further includes a removable cap sealingly located on said outlet.

* * * * *